United States Patent [19]
Graham, Jr. et al.

[11] 4,095,591
[45] Jun. 20, 1978

[54] COMPRESSION SCREW SYSTEM

[75] Inventors: Charles M. Graham, Jr.; Thomas L. Craig, both of Memphis, Tenn.

[73] Assignee: Richards Manufacturing Co., Inc., Memphis, Tenn.

[21] Appl. No.: 763,031

[22] Filed: Jan. 27, 1977

[51] Int. Cl.² .................. A61B 17/18; A61F 5/04
[52] U.S. Cl. .................. 128/92 BB; 128/92 EB; 128/92 EC
[58] Field of Search ............ 128/92 BB, 92 BA, 92 B, 128/92 BC, 92 R, 92 D, 92 G, 92 EB, 92 EC, 92 E, 83

[56] References Cited
U.S. PATENT DOCUMENTS 2,187,852   1/1940   Friddle .................. 128/92 EC

OTHER PUBLICATIONS

"Richards Compression Hip Screw," Richards Mfg. Co. Catalog, 1966, pp. 72–73.

*Primary Examiner*—Ronald L. Frinks
*Attorney, Agent, or Firm*—John R. Walker, III

[57] ABSTRACT

An extension is provided for being nonrotatably fixed to a lag screw that is to be anchored to the head of a femur or other bone in a manner so as to allow compression to be applied to a fracture. The extension extends outward of the bone when attached to the lag screw and when the lag screw is anchored to the bone to allow a compression plate to be easily positioned thereon. The cross-section of the extension is substantially the same as the cross-section of the lag screw to allow the compression plate to be easily and quickly passed onto the lag screw from the extension once the compression plate has been positioned on the extension.

10 Claims, 16 Drawing Figures

COMPRESSION SCREW SYSTEM

BACKGROUND OF THE PRIOR ART

1. Field of the Invention

This invention relates to compression screw systems for applying compression to a fractured bone to aid in the healing thereof.

2. Description of the Prior Art

Compression screw systems, in general, consist of a lag screw for being anchored to the bone on one side of a fracture, a compression plate for being attached to the bone on the other side of the fracture, and a compression screw for extending from the compression plate to the lag screw to allow compression to be applied between the lag screw and the compression plate. The compression plate is usually adapted to fit over a portion of the lag screw to prevent the lag screw from rotating when the compression screw is screwed thereinto. More specifically, the lag screw is usually provided with a longitudinally directed keyway, and the compression plate is usually provided with a hollow barrel member for sliding over the lag screw, the barrel member being provided with a longitudinally directed key for co-acting with the longitudinally directed keyway of the lag screw to non-rotatably attach the lag screw and the compression plate together. However, this system is disadvantageous in that it is difficult and time consuming to fit the barrel member of the compression plate over the lag screw with the key of the barrel member properly engaging the keyway of the lag screw, especially since the end of the lag screw does not extend outward of the bone, but rather usually ends about one-half inch within the bone, thus requiring the surgeon to fit the two parts together in a trial-and-error type manner. Attempts have heretofore been made towards overcoming the above disadvantages and problems. For example, one attempt has been to screw an elongated extension member having a cross-section smaller than the cross-section of the lag screw into the end of the lag screw after the lag screw has been anchored to the bone to allow the surgeon to place the barrel member of the compression plate over the extension member and to merely slide the barrel member along the extension member to the lag screw. While this attempt does alleviate some of the disadvantages heretofore discussed, it does not completely overcome such problems since the surgeon must still fit the two pieces together in a substantially trial-and-error type method. Rather, this attempt merely serves to reduce the amount of trial-and-error in aligning the aperture of the barrel member with the outside of the lag screw. Another attempt has been to recess the key of the barrel member away from the forward end of the barrel member so as to take the necessary aligning steps into two distinct steps: first, aligning the aperture of the barrel member of the compression plate with the outside of the lag screw; next, aligning the key of the barrel member with the keyway of the lag screw. However, such an attempt does not entirely overcome the above problems and disadvantages since the surgeon must still fit the two parts together in substantially a trial-and-error type method.

SUMMARY OF THE INVENTION

The present invention is directed towards overcoming the problems and disadvantages of prior compression screw systems. The concept of the present invention is to provide means for allowing the compression plate of a compression screw system to be positively aligned with the lag screw thereof by a surgeon without requiring trial-and-error type methods to be performed. The compression screw system of the present invention includes a lag screw for being anchored to the bone on one side of a fracture thereof; compression plate means for being attached to the lag screw and to the bone on the other side of the fracture thereof to allow compression to be applied to the bone between the two sides of the fracture thereof to aid in the healing of the fracture, the compression plate means including a barrel member having an aperture therethrough for passing over one end of the lag screw and for being nonrotatably attached to the lag screw, the compression means also including a body member for being fixedly attached to the bone; and barrel guide means for guiding the barrel member of the compression plate means onto the lag screw, the barrel guide means including an extension member being of sufficient length so as to extend outward of the bone when attached to the lag screw and when the lag screw is anchored to the bone, the extension member being substantially the same in cross-section as one end of the lag screw so that the barrel portion of the compression means will pass thereover.

DESCRIPTION OF THE PREFERRED EMBODIMENT

Figure 1:
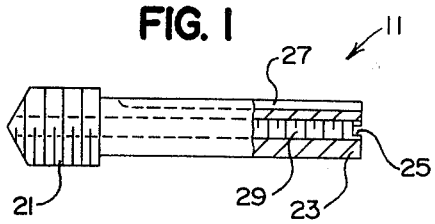
FIG. 1 is a partially sectional side elevational view of the lag screw of the compression screw system of the present invention.

The compression screw system of the present invention is for use in applying compression to a fractured bone and particularly to the fractured neck N of a femur F to aid in the healing thereof. (See, in general, FIGS. 13, 14, 15 and 16). While the compression screw system of the present invention can be used to apply compression to a fracture in any bone (e.g., a supercondylar fracture) wherein a lag screw is anchored to the bone on one side of a fracture, a compression plate is anchored to the bone on the other side of the fracture, and means such as a compression screw is used to apply compression between the lag screw and the compression plate and, therefore, to the fracture, the present invention is particularly adapted for applying compression to the fractured neck N of a femur F and will now be described as being so used. It will of course be apparent to those skilled in the art how to use the compression screw system of the present invention to apply compression to other fractured bones. The compression screw system of the present invention includes, in general, a lag screw 11 for being anchored to the head H of the femur F, a compression plate means 13 for being attached to the lag screw 11 and to the shaft S of the femur F, a barrel guide means 15 for guiding a portion of the compression plate means 13 onto the lag screw 11, a screw insertion wrench 17 for use in screwing the lag screw 11 into the head H of the femur F, and compression screw means 19 for applying compression between the lag screw 11 and the compression plate means 13 to thereby apply compression between the head H and the shaft S of the femur F.

Figure 2:
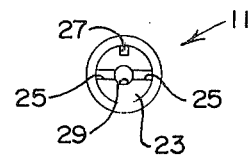
FIG. 2 is an end elevational view of the lag screw of the compression screw system of the present invention.

The lag screw 11 preferably consists of an elongated, rigid member having a threaded first end 21 for being anchored to the head H of the femur F by being screwed thereto. The lag screw 11 also preferably includes a second end 23 having a transverse keyway 25 thereacross as clearly shown in FIGS. 1 and 2. Additionally, the lag screw 11 preferably includes a longitudinally directed keyway 27 extending from the second end 23 thereof towards the first end 21 thereof as shown in FIGS. 1 and 2. Also, the lag screw 11 preferably includes a threaded aperture 29 in the second end 23 thereof as shown in FIGS. 1 and 2. It should be noted that the aperture 29 may extend completely through the lag screw 11 from the first and 23 thereof to the second end 21 thereof as shown in FIG. 1. The lag screw 11 is preferably made of metal such as stainless steel and is preferably provided in various sizes for reasons well known to those skilled in the art.

Figure 9:
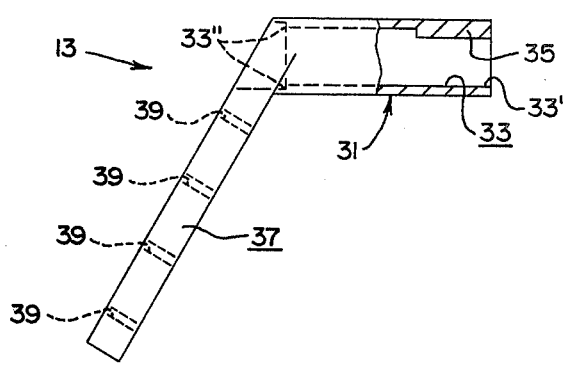
FIG. 9 is a partially sectional side elevational view of the compression plate means of the compression screw system of the present invention.
Figure 10:
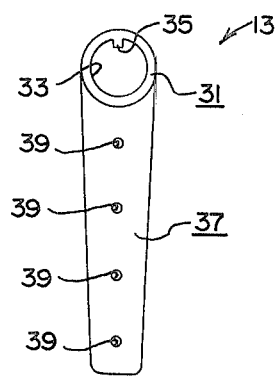
FIG. 10 is an end elevational view of the compression plate means of the compression screw system of the present invention.
Figure 11:
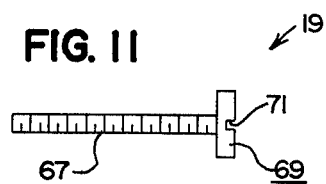
FIG. 11 is a side elevational view of the compression screw means of the compression screw system of the present invention.
Figure 12:
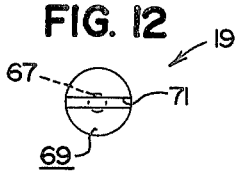
FIG. 12 is an end elevational view of FIG. 11.
Figure 16:
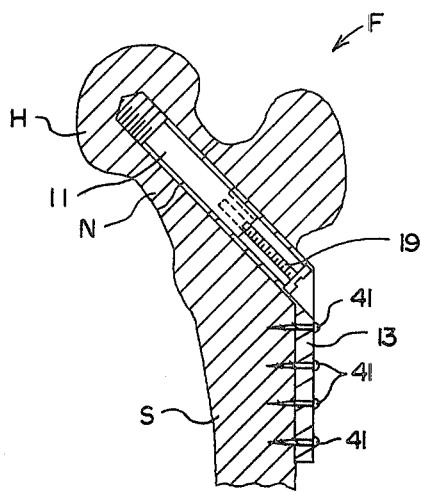
FIG. 16 is a sectional view similar to FIGS. 13, 14 and 15 but showing the compression plate of the compression screw system of the present invention positioned on the lag screw and attached to the shaft of the femur.

The compression plate means 13 preferably includes a barrel member 31 having an aperture 33 therethrough of a size larger than the outer circumference of the lag screw 11 for receiving at least a portion of the second end 23 of the lag screw 11 (see, in general, FIGS. 9 and 10). The barrel member 31 also preferably includes a longitudinally directed key 35 provided in at least a portion of the aperture 33 for coacting with the longitudinally directed keyway 27 of the lag screw 11 to nonrotatably join the compression plate means 13 and the lag screw 11 together. Preferably, the longitudinally directed key 35 is provided substantially adjacent the forward end 33' of the aperture 33 as shown in FIG. 9. A shoulder-like portion 33" is preferably provided adjacent the rearward end of the aperture 33 for reasons which will hereinafter become apparent. The compression plate means 13 also preferably includes a body portion 37 for being selectively fixedly attached to the shaft S of the femur F. The body portion 37 is preferably provided with a plurality of apertures 39 as shown in FIGS. 9 and 10 for allowing the compression plate means 13 to be attached to the shaft S of the femur F by way of screws 41 or the like as shown in FIG. 16. The compression plate means 13 is preferably constructed of a metal such as stainless steel and is preferably constructed in various shapes and sizes for reasons well known to those skilled in the art.

Figure 3:
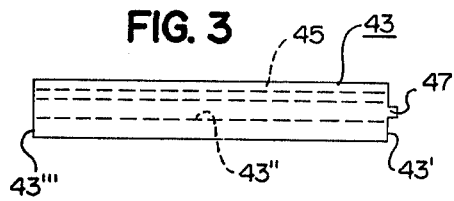
FIG. 3 is a side elevational view of the extension member of the barrel guide means of the compression screw system of the present invention.
Figure 4:
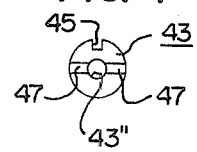
FIG. 4 is an end elevational view of FIG. 3.
Figure 5:
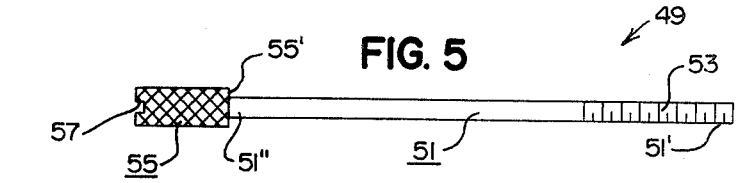
FIG. 5 is a side elevational view of the retaining screw member of the barrel guide means of the compression system of the present invention.
Figure 6:
FIG. 6 is an end elevational view of FIG. 5.
Figure 14:
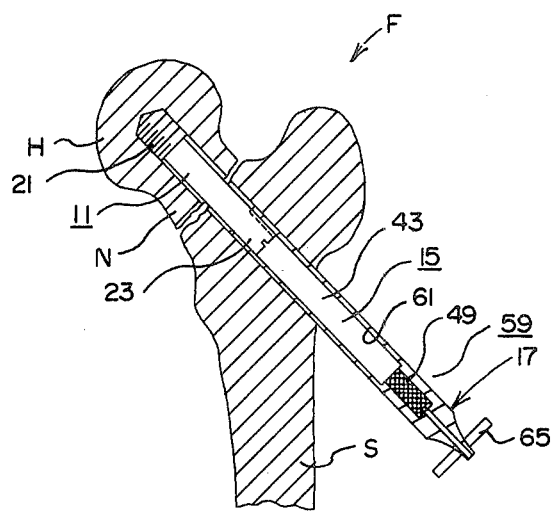
FIG. 14 is a sectional view similar to FIG. 13 but showing the lag screw of the compression screw system of the present invention being inserted into the hole.
Figure 15:
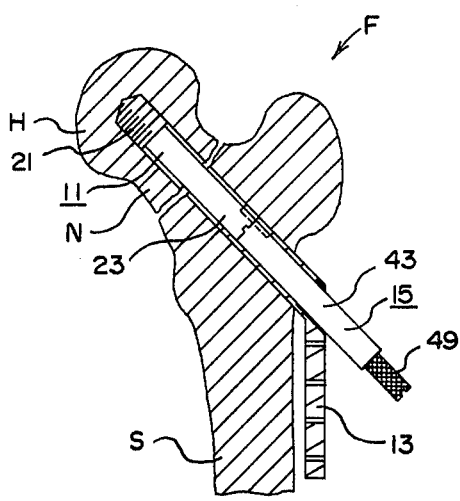
FIG. 15 is a view similar to FIGS. 13 and 14 but showing the compression plate being positioned on the lag screw.

The barrel guide means 15 preferably includes a hollow extension member 43 for attachment to the second end 23 of the lag screw 11. The extension member 43 is of sufficient length so as to extend outward of the shaft S of the femur F when attached to the lag screw 11 and when the lag screw 11 is anchored to the head H of the femur as shown in FIGS. 14 and 15. The extension member 43 is preferably provided with a longitudinally directed keyway 45 provided along its entire length as clearly shown in FIGS. 3 and 4. Also, the extension member 43 preferably has an outer circumference or outer diameter, substantially the same as the outer circumference or outer diameter, of the second end 23 of the lag screw 11 for allowing the barrel member 31 of the compression plate means 13 to pass thereover. That is, the cross-section of the extension member 43 is preferably substantially the same as the cross-section of the second end 23 of the lag screw 11 so that when the lag screw 11 and barrel guide means 15 are attached together, they will form an elongated member having substantially the same outer circumference from at least the second end 23 of the lag screw 11 to the outer end of the extension member 43 as shown in FIGS. 14 and 15. The barrel guide means 15 also includes attachment means for nonrotatably attaching the extension member 43 to the lag screw 11 with the longitudinally directed keyway 45 of the extension member 43 being substantially aligned with the longitudinally directed keyway 27 of the lag screw 11. The attachment means preferably includes a pair of transverse keys 47 attached to the rearward end 43' of the extension member 43 as clearly shown in FIGS. 3 and 4 for coacting with the transverse keyways 25 of the lag screw 11. (See, in general, FIGS. 13, 14 and 15). The attachment means also preferably includes a retaining screw member 49 for coacting with the threaded aperture 29 of the lag screw 11 to attach the extension member 43 to the lag screw 11. (See, in general, FIGS. 13, 14 and 15). More specifically, the retaining screw member 49 includes an elongated body portion 51 of a size which allows it to pass through the hollow extension member 43 and which includes a threaded portion 53 on the forward end 51' thereof for engagement with the threaded aperture 29 of the lag screw 11. A head portion 55 is fixedly attached to the rearward end 51" of the elongated body portion 51 for allowing the retaining screw member 49 to be manually tightened onto the lag screw 11. Head portion 55 is larger than body portion 51 to provide a shoulder 55' adjacent the juncture with body portion 51. Also, head portion 55 is larger than the bore 43" through extension member 43 so that shoulder 55' engages the end 43''' of extension member 43 to retain the extension member in attachment with the lag screw 11. A transverse slot 57 may be provided across the head portion 55 for allowing a screwdriver or the like to be used to tighten the retaining screw member 49 onto the lag screw 11. Also, the head portion 55 may be provided with a rough outer surface in any manner apparent to those skilled in the art (e.g., by being knurled) to allow the head portion 55 to be easily manually gripped to allow the retaining screw member 49 to be tightened onto the lag screw 11.

Figure 7:
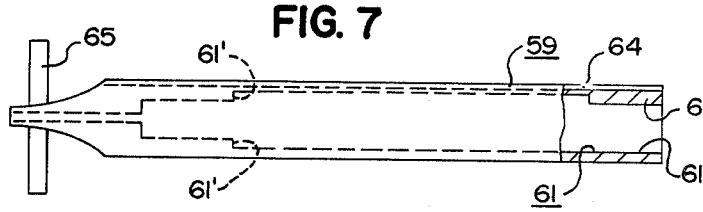
FIG. 7 is a partially sectional side elevational view of the screw insertion wrench of the compression screw system of the present invention.
Figure 8:
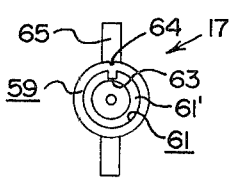
FIG. 8 is an end elevational view of the screw insertion wrench of the compression hip screw system of the present invention.

The screw insertion wrench 17 preferably includes body member 59 having a socket 61 therein for receiving the barrel guide means 15 and at least a portion of the lag screw 11 as shown in FIG. 14. The socket 61 is preferably provided with a shoulder portion 61' (see, in general, FIG. 7) to act as a stop for the end 43''' of the extension member 43 to properly position the screw insertion wrench 17 and the lag screw 11 in the socket 61 as shown in FIG. 14. The body member 59 also preferably includes a longitudinally directed key 63 provided in the socket 61 for coacting with the longitudinally directed keyway 27 of the lag screw 11 to cause the lag screw 11 to turn with the body member 59 in a manner apparent to those skilled in the art. The key 63 is preferably provided adjacent the forward end 61'' of the socket 61. (See FIG. 7). The screw insertion wrench 17 also may include a handle member 65 fixedly attached to the body member 59 for aiding in manually turning the body member 59. Additionally, the screw insertion wrench 17 may include indicia means such as a groove 64 in the outer surface of the body member 59 for reasons which will hereinafter become apparent.

The compression screw means 19 preferably includes an elongated threaded body member 67 for coacting with the threaded aperture 29 of the lag screw 11 and for extending through the aperture 33 in the barrel member 35 of the compression plate means 13. The compression screw means 19, also preferably includes a head portion 69 fixedly attached to the body member 67. The head portion 69 preferably has an outer circumference too large to pass completely through the aperture 33 of the barrel member 31 of the compression plate means 13 so that the compression screw means 19 will fixedly attach the lag screw 11 and the compression plate means 13 together so as to allow compression to be applied between the head H and the shaft S of the femur F to aid in the healing of the fracture in the neck N of the femur F. More specifically, the head portion 69 will rest against the shoulder-like portion 33'' of the aperture 33 when inserted through the aperture 33 and when the body member 67 is screwed into the aperture 29 of the lag screw 11 as shown in FIG. 16. The head portion 69 of the compression screw means 19 may be provided with a transverse slot 71 for allowing a screwdriver or the like to be utilized in screwing the screw compression means 19 into the aperture 29 of the lag screw 11.

Figure 13:
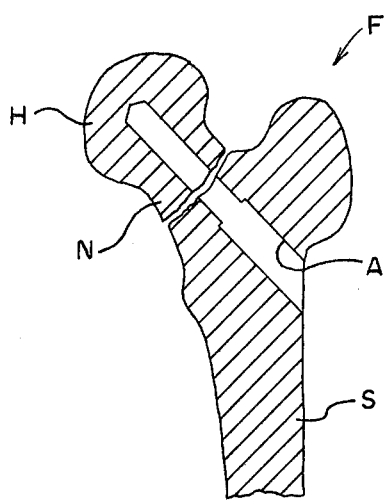
FIG. 13 is a sectional view of the head, fractured neck, and a portion of the shaft of a femur showing a hole reamed through the shaft, neck and into the head thereof for receiving portions of the compression screw system of the present invention.

To use the compression screw system of the present invention to apply compression to the fractured neck N of a femur F, the first step is to ream an aperture A into the head H of the femur F through the shaft S and neck N of the femur as shown in FIG. 13. The aperture A may be made in any manner well known to those skilled in the art and may be of any shape and dimension known to those skilled in the art. Next, the barrel guide means 15 is fitted onto the second end 23 of the lag screw 11 with the pair of transverse keys 47 of the extension member 43 engaging the transverse keyway 25 of the second end 23 of the lag screw and with the threaded portion 53 of the body portion 51 of the retaining screw member 49 engaging the threaded aperture 29 of the lag screw to thereby fixedly and nonrotatably attach the lag screw 11 and the barrel guide means 15 together with the longitudinally directed keyways 27, 45 of the lag screw 11 and the extension member 43 of the barrel guide means 15 aligned with one another. The screw insertion wrench 17 is then placed over the barrel guide means 15 and at least a portion of the lag screw 11 so that the longitudinally directed key 63 of the screw insertion wrench 17 will engage the longitudinally directed keyway 27 of the lag screw 11. The lag screw 11 is then inserted into the aperture A and screwed into the head H of the femur F with the aid of the screw insertion wrench 17. The lag screw 11 is preferably screwed into the femur F until the groove 64 of the screw insertion wrench 17 signifies that the lag screw 11 is properly positioned in the head H of the femur F with the keyway 27 thereof directed upwards. After the lag screw 11 is thus properly anchored to the head H of the femur F the screw insertion wrench is removed from the lag screw 11 and the barrel guide means 15. Next, the barrel member 31 of the compression plate means 13 is slid onto the extension member 43 of the barrel guide means 15 with the longitudinally directed key 35 thereof sliding along the longitudinally directed keyway 45 of the extension member 43 as shown in FIG. 15. The compression plate means 13 is then positioned with the body portion 37 thereof against the shaft S of the femur and with the longitudinally directed key 35 of the barrel member 31 engaging the longitudinally directed keyway 27 of the lag screw 11. The body portion 37 of the compression plate means 13 is then anchored to the shaft S of the femur F by way of the screws 41 as shown in FIG. 16 and the barrel guide means 15 is removed from the lag screw 11. The compression screw means 19 is then screwed into the threaded aperture 29 of the lag screw 11 with the head portion 69 thereof engaging the shoulder-like portion 33'' of the aperture 33 of the barrel member 31 to apply compression between the head H and the shaft S of the femur F.

Although the invention has been described and illustrated with respect to a preferred embodiment thereof, it is not to be so limited since changes and modifications may be made therein which are within the full intended scope of the invention. For example, rather than nonrotatably attaching the lag screw 11, compression plate means 13, barrel guide means 15 and screw insertion wrench 17 together by way of keys and keyways, they may be nonrotatably attached together by way of hex-like boss members and sockets or the like, as will be apparent to those skilled in the art.

We claim:

1. An improvement in a compression screw system of the type where a lag screw is adapted to be anchored to a bone on one side of a fracture, where a compression plate means having a hollow barrel member provided with means for coacting with said lag screw to nonrotatably join said plate means and said lag screw is adapted to be positioned on the bone on the other side of the fracture, and where a compression screw means is positioned between said lag screw and said plate means for fixedly attaching said lag screw and said plate means together so as to allow compression to be applied between said lag screw and said plate means to aid in the healing of the fracture in the bone, wherein said improvement comprises: barrel guide means for guiding said barrel member of said plate means onto said lag screw, said barrel guide means including an extension member for attachment to said lag screw, said extension member being of sufficient length so as to extend outward of the bone when attached to said lag screw and when said lag screw is anchored to the bone, and being of a size for allowing said barrel member of said compression plate means to pass thereover, said barrel guide means including attachment means for attaching said extension member to said lag screw, said attachment means including means attached to said extension member in a position offset from the longitudinal axis of said extension member for coacting with said lag screw to nonrotatably attach said extension member to said lag screw.

2. An improvement in a compression screw system of the type where a lag screw is adapted to be anchored to a bone on one side of a fracture, where a compression plate means having a hollow barrel member provided with means for coacting with said lag screw to nonrotatably join said plate means and said lag screw is adapted to be positioned on the bone on the other side of the fracture, and where compression screw means is positioned between said lag screw and said plate means for fixedly attaching said lag screw and said plate means together so as to allow compression to be applied between said lag screw and said plate means to aid in the healing of the fracture in the bone, said lag screw including a first end for being fixedly attached to the bone and including a second end for being nonrotatably attached to said plate means, wherein said improvement comprises: barrel guide means for guiding said barrel member of said plate means onto said lag screw, said barrel guide means including an extension member for attachment to said lag screw, said extension member being of sufficient length so as to extend outward of the bone when attached to said lag screw and when said lag screw is anchored to the bone, and being of a size for allowing said barrel member of said compression plate means to pass thereover, said barrel guide means including attachment means for nonrotatably attaching said extension member to said lag screw; and providing a transverse keyway across said second end of said lag screw, said attachment means of said barrel guide means including at least one transverse key attached to said extension member for coacting with said transverse keyway of said lag screw to nonrotatably attach said extension member of said barrel guide means to said lag screw.

3. The improvement of claim 2 in which said attachment means of said barrel guide means includes a retaining screw member for attaching said extension member of said barrel guide means to said lag screw.

4. A system for applying compression to a fractured bone, said system comprising:
(a) a lag screw for being anchored to the bone on one side of the fracture, said lag screw including a first end for being selectively anchored to the bone and including a second end;
(b) compression plate means for being selectively attached to said second end of said lag screw and to the bone on the other side of the fracture to allow compression to be applied between said lag screw and said compression plate means to aid in the healing of the fracture in the bone, said compression plate means including a barrel member having an aperture therethrough for passing over said second end of said lag screw, said compression plate means including means for nonrotatably attaching said barrel member to said lag screw, said compression plate means including a body member for being fixedly attached to the bone; and
(c) barrel guide means for guiding said barrel member of said compression plate means onto said second end of said lag screw, said barrel guide means including an extension member for attachment to said second end of said lag screw, said extension member being of sufficient length so as to extend outward of the bone when attached to said lag screw and when said lag screw is anchored to the bone, said extension member having the same outer circumference as said second end of said lag screw so that said barrel portion of said compression plate means will pass thereover and will be aligned with said second end of said lag screw when passed over said extension member.

5. A system for applying compression to a fractured bone, said system comprising:
(a) a lag screw for being anchored to the bone on one side of the fracture, said lag screw including a first end for being selectively anchored to the bone and including a second end, said lag screw including a longitudinally directed keyway extending from said second end thereof towards said first end thereof;
(b) compression plate means for being selectively attached to said second end of said lag screw and to the bone on the other side of the fracture to allow compression to be applied between said lag screw and said compression plate means to aid in the healing of the fracture in the bone, said compression plate means including a barrel member having an aperture therethrough for passing over said second end of said lag screw, said compression plate means including means for nonrotatably attaching said barrel member to said lag screw, said means for nonrotatably attaching said barrel member to said lag screw including a longitudinally directed key provided in said aperture of said barrel member for coacting with said longitudinally directed keyway of said lag screw to nonrotatably join said compression plate means and said lag screw, said compression plate means including a body member for being fixedly attached to the bone; and
(c) barrel guide means for guiding said barrel member of said compression plate means onto said second end of said lag screw, said barrel guide means including an extension member for attachment to said second end of said lag screw, said extension member being of sufficient length so as to extend outward of the bone when attached to said lag screw and when said lag screw is anchored to the bone, said extension member having substantially the same outer circumference as said second end of said lag screw so that said barrel portion of said compressing plate means will pass thereover, said extension member of said barrel guide means having a longitudinally directed keyway provided along its entire length for allowing said barrel member of said compression plate means to pass thereover with said longitudinally directed key of said barrel member passing through said longitudinally directed keyway of said extension means.

6. The system of claim 5 in which said second end of said lag screw has a transverse keyway thereacross, and in which said barrel guide means includes attachment means for nonrotatably attaching said extension member to said lag screw with said longitudinally directed keyway of said extension member being substantially aligned with said longitudinally directed keyway of said lag screw, said attachment means of said barrel guide means including a transverse key attached to one end of said extension member for coacting with said transverse keyway of said lag screw to nonrotatably attach said extension member to said lag screw.

7. The system of claim 6 in which said attachment means of said barrel means includes a retaining screw member for passing through said extension member and for being screwed into said lag screw to attach said extension member to said lag screw.

8. The system of claim 7 in which is included a screw insertion wrench for use in screwing said lag screw into bone, said screw insertion wrench including a body member having an aperture therein for receiving said barrel guide means and at least a portion of said lag screw, said body member including a longitudinally directed key for coacting with said longitudinally directed keyway of said lag screw to cause said lag screw to turn with said body member.

9. The system of claim 8 in which said lag screw includes a threaded aperture in said second end thereof, and in which is included a compression screw means for coacting with said threaded aperture in said lag screw and with said compression plate means to fixedly attach said compression plate means to said lag screw.

10. A system for applying compression to the fractured neck of a femur, said system comprising:
(a) a lag screw including a threaded first end for being anchored to the head of the femur, said lag screw including a second end having a transverse keyway thereacross, said lag screw including a longitudinally directed keyway extending from said second end thereof towards said first end thereof and including a threaded aperture in said second end thereof;
(b) a compression plate means including a barrel member for being nonrotatably joined to said lag screw, said barrel member having an aperture therethrough of a size larger than the outer circumference of said lag screw for receiving at least a portion of said second end of said lag screw and having a longitudinally directed key provided in said aperture for coacting with said longitudinally directed keyway of said lag screw to nonrotatably join said compression plate means and said lag screw, said compression plate means including a body portion for being selectively fixedly attached to the shaft of the femur;
(c) barrel guide means for guiding said barrel portion of said compression plate member onto said lag screw, said barrel guide means including a hollow extension member for attachment to said second end of said lag screw, said extension member being of sufficient length so as to extend outward of the shaft of the femur when attached to said lag screw and when said lag screw is anchored to the head of the femur, said extension member having a longitudinally directed keyway provided along its entire length and having an outer circumference substantially the same as the outer circumference of said second end of said lag screw for allowing said barrel member of said compression plate means to pass thereover, said barrel guide means including attachment means for nonrotatably attaching said extension member to said lag screw with said longitudinally directed keyway of said extension member being substantially aligned with said longitudinally directed keyway of said lag screw, said attachment means including a pair of transverse keys attached to one end of said extension member for coacting with said transverse keyway of said lag screw to nonrotatably attach said extension member to said lag screw, said attachment means including a retaining screw member for passing through said hollow extension member to coact with said threaded aperture of lag screw and to attach said extension member to said lag screw;
(d) a screw insertion wrench for use in screwing said lag screw into the head of the femur, said screw insertion wrench including a body member having a socket therein for receiving said barrel guide means and at least a portion of said lag screw, said body member including a longitudinally directed key for coacting with said longitudinally directed keyway of said lag screw to cause said lag screw to turn with said body member, said screw insertion wrench including a handle member fixedly attached to said body member for use in manually turning said body member; and
(e) compression screw means including an elongated threaded body member for coacting with said threaded aperture of said lag screw and for extending through said aperture of said barrel member of said compression plate means, said compression screw means including a head portion being too large to pass through said aperture of said barrel member of said compression plate means so that said compression screw means will fixedly attach said lag screw and said compression plate means together so as to allow compression to be applied between the head and the shaft of the femur to aid in the healing of a fracture in the neck of the femur.

* * * * *